(12) United States Patent
Fariabi (10) Patent No.: US 6,287,292 B1
(45) Date of Patent: *Sep. 11, 2001

(54) GUIDEWIRE WITH A VARIABLE STIFFNESS DISTAL PORTION

(75) Inventor: Sepehr Fariabi, Fremont, CA (US)

(73) Assignee: Advanced Cardiovascular Systems, Inc., Santa Clara, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/287,703

(22) Filed: Apr. 6, 1999

Related U.S. Application Data

(62) Division of application No. 08/634,208, filed on Apr. 18, 1996, now Pat. No. 5,931,819.

(51) Int. Cl.[7] .................................................. A61M 25/00
(52) U.S. Cl. ........................................... 604/531; 604/500
(58) Field of Search ............................. 128/898; 604/500, 604/28, 526, 528, 530–2, 523; 600/433, 434

(56) References Cited

U.S. PATENT DOCUMENTS

| 4,215,703 | 8/1980 | Wilson . |
|---|---|---|
| 4,283,233 | 8/1981 | Goldstein et al. . |
| 4,516,972 | 5/1985 | Samson . |
| 4,538,622 | 9/1985 | Samson et al. . |
| 4,543,090 | 9/1985 | McCoy . |
| 4,554,929 | 11/1985 | Samson et al. . |
| 4,616,652 | 10/1986 | Simpson . |
| 4,748,986 | 6/1988 | Morrison et al. . |
| 4,777,799 | 10/1988 | McCoy et al. . |
| 4,881,981 | 11/1989 | Thoma et al. . |
| 4,917,102 | 4/1990 | Miller et al. . |
| 4,925,445 | 5/1990 | Sakamoto et al. . |
| 4,935,068 | 6/1990 | Duerig . |
| 4,944,727 | * 7/1990 | McCoy .................................. 604/95 |
| 4,984,581 | 1/1991 | Stice . |
| 4,991,602 | 2/1991 | Amplatz et al. . |
| 5,025,799 | 6/1991 | Wilson . |
| 5,055,101 | 10/1991 | McCoy . |
| 5,069,226 | 12/1991 | Yamauchi et al. . |
| 5,114,402 | 5/1992 | McCoy . |
| 5,120,308 | 6/1992 | Hess . |
| 5,135,504 | 8/1992 | McLees . |
| 5,143,085 | 9/1992 | Wilson . |
| 5,211,183 | 5/1993 | Wilson . |
| 5,213,111 | 5/1993 | Cook et al. . |
| 5,230,348 | 7/1993 | Ishibe et al. . |
| 5,238,004 | 8/1993 | Sahatjian et al. . |

(List continued on next page.)

FOREIGN PATENT DOCUMENTS

| 310295 | 4/1989 | (EP) . |
|---|---|---|
| 62-20827 | 8/1987 | (JP) . |
| WO 90/03760 | 4/1990 | (WO) . |
| WO 94/12089 | 6/1994 | (WO) . |
| WO 95/06494 | 3/1995 | (WO) . |

Primary Examiner—Anhtuan T. Nguyen
Assistant Examiner—Michael M Thompson
(74) Attorney, Agent, or Firm—Heller Ehrman White & McAuliffe LLP (57) ABSTRACT

A guidewire having a core section formed of a NiTi alloy which is in an austenite phase when being manufactured but which is converted to the martensite phase at operating (body) temperature (37° C.) and can be transformed to an austenite phase by heating to a temperature above body temperature but below 50° C. When in the austenite phase, the core section is at a high strength level which ensures the tracking of a catheter over the guidewire within a patient's body lumen. In one preferred embodiment the core section is heated by electrical resistance or inductance.

2 Claims, 5 Drawing Sheets

U.S. PATENT DOCUMENTS

| | | |
|---|---|---|
| 5,243,996 | 9/1993 | Hall . |
| 5,334,168 | 8/1994 | Hemmer . |
| 5,341,818 | 8/1994 | Abrams et al. . |
| 5,357,979 | 10/1994 | Imran . |
| 5,409,015 * | 4/1995 | Palermo ................................ 128/772 |
| 5,411,476 | 5/1995 | Abrams et al. . |
| 5,423,771 | 6/1995 | Imran . |
| 5,542,434 | 8/1996 | Imran et al. . |
| 5,938,623 * | 8/1999 | Quiachon et al. ................... 600/585 |

* cited by examiner

GUIDEWIRE WITH A VARIABLE STIFFNESS DISTAL PORTION

This is a divisional Ser. No. 08/634,208 filed Apr. 18, 1996, now U.S. Pat. No. 5,931,819 incorporated by reference.

BACKGROUND OF THE INVENTION

This invention relates to the field of medical devices, and more particularly to guiding means such as a guidewire for advancing a catheter within a body lumen to perform a procedure such as percutaneous transluminal coronary angioplasty (PTCA).

In a typical PTCA procedure a guiding catheter having a preformed distal tip is percutaneously introduced into the cardiovascular system of a patient by means of a conventional Seldinger technique and advanced therein until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the balloon is inflated one or more times to a predetermined size with radiopaque liquid at relatively high pressures (e.g., greater than 4 atmospheres) to compress the arteriosclerotic plaque of the lesion against the inside of the artery wall and to otherwise expand the inner lumen of the artery. The balloon is then deflated so that blood flow resumes through the dilated artery and the dilatation catheter can be removed therefrom.

Conventional guidewires for angioplasty and other vascular procedures usually comprise an elongated core member with the distal portion of the core member having one or more tapered sections and a flexible body such as a helical coil disposed about the distal portion of the core member. A shapable member, which may be the distal extremity of the core member or a separate shaping ribbon which is secured to the distal extremity of the core member extends through the flexible body and is secured to a rounded plug at the distal end of the flexible body. Torquing means are provided on the proximal end of the core member to rotate, and thereby steer, the guidewire while it is being advanced through a patient's vascular system.

Further details of guidewires can be found in U.S. Pat. Nos. 4,516,972 (Samson); 4,538,622 (Samson, et al.); 4,554,929 (Samson, et al.); 4,616,652 (Simpson), 4,748,986 (Morrison et al.) 5,135,504 (Abrams); 5,341,818 (Abrams et al. And 5,411,476 (Abrams et al) which are hereby incorporated herein in their entirety by reference thereto.

A major requirement for guidewires and other intraluminal guiding members, whether they be solid wire or tubular members, is that they have sufficient column strength to be pushed through a patient's vascular system or other body lumen without kinking. However, they must also be flexible enough to pass through tortuous passageways without damaging the blood vessel or other body lumen through which they are advanced. Efforts have been made to improve both the strength and flexibility of guidewires in order to make them more suitable for their intended uses, but these two properties tend to be diametrically opposed to one another in that an increase in one usually involves a decrease in the other.

The prior art makes reference to the use of alloys such as NITINOL (Ni—Ti alloy) which have shape memory and/or superelastic or pseudoelastic characteristics in medical devices which are designed to be inserted into a patient's body. The shape memory characteristics allow the prior art devices to be deformed while in the martensite phase to facilitate their insertion into a body lumen or cavity and then be heated within the body to transform the metal to the austenite phase so that the device returns to its remembered shape. Superelastic characteristics on the other hand generally allow the metal to be deformed and restrained in the deformed condition to facilitate the insertion of the medical device containing the metal into a patient's body, with such deformation causing the phase transformation, e.g. austenite to martensite. Once within the body lumen the restraint on the superelastic member can be removed, thereby reducing the stress therein so that the superelastic member can return to its original undeformed shape by the transformation back to the original austenite phase. In other applications, the stress induced austenite to martensite transformation is utilized to minimize trauma while advancing a medical device such as a guidewire within a patient's body lumen.

Alloys have shape memory/superelastic characteristics generally have at least two phases, a martensite phase, which has a relatively low strength and which is stable at relatively low temperatures, and an austenite phase, which has a relatively high strength and which is stable at temperatures higher than the martensite phase.

Shape memory characteristics are imparted to the alloy by heating the metal at a temperature above body temperature, preferably between about 40° to about 60° C. while the metal is kept in a constrained shape and then cooled to ambient temperature. The cooling of the alloy to ambient temperature causes at least part of the austenite phase to transform to the martensite phase which is more stable at this temperature. the constrained shape of the metal during this heat treatment is the shape "remembered" when the alloy is reheated to these temperatures causing the transformation of the martensite phase to the austenite phase. The metal in the martensite phase may be plastically deformed to facilitate the entry thereof into a patient's body. The metal will remain in the "remembered" shape even when cooled to a temperature below the transformation temperature back to the martensite phase, so it must be reformed into a more usable shape, if necessary. Subsequent heating of the deformed martensite phase to a temperature above the martensite to austenite transformation temperature causes the deformed martensite phase to transform to the austenite phase and during this phase transformation the metal reverts back to its remembered shape.

The prior methods of using the shape memory characteristics of these alloys in medical devices intended to be placed within a patient's body presented operational difficulties. For example, with shape memory alloys having a martensite phase which is stable at a temperature below body temperature, it was frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensite-to-austenite transformation temperatures well above body temperature, the devices could be introduced into a patient's body with little or no problem, but they usually had to be heated to the martensite-to-austenite transformation temperature which was frequently high enough to cause tissue damage and very high levels of pain.

When stress is applied to a specimen of a metal such as NITINOL exhibiting superelastic characteristics at a temperature at or above which the transformation of martensite phase to the austenite phase is complete, the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress is necessary to cause further deformation. The martensitic metal first yields elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e., there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity.

SUMMARY OF THE INVENTION

The present invention is directed to improve guidewires or guiding members, wherein a core section which is manufactured in an austenite phase to facilitate manufacturing such as centerless grinding or any other desirable shaping or machining and which is then transformed at least partially into a lower strength martensite phase to improve its flexibility and to facilitate its advancement within the patient.

The guidewire of the invention generally has a high strength proximal core section, an intermediate core section formed at least in part of a NiTi alloy which has a significant level of martensite phase at body temperature (approximately 37° C.) but which transforms to the higher strength austenite phase at a temperature above body temperature. A distal core section may have a flexible body, such as a helical coil, disposed about and secured to at least part of the distal core section.

Generally, the intermediate core section should have about 10% to about 75%, preferably about 25% to about 50% martensite at body temperature. An intermediate core section which is 100% martensite phase can have inadequate strength to be readily pushed through body lumens in some instances. Preferably, the temperature at which the transformation of the martensite to austenite is complete, i.e. $A_f$, should not be high enough to cause significant pain or tissue damage. The conversion to the austenite phase should be nearly complete, i.e. at least 75%, for best results. Reference herein to percent metallic phase is to weight percent unless noted otherwise.

Means are provided to heat the intermediate core section while it is disposed within the patient to transform martensite phase in the NiTi alloy thereof to the austenite phase. Preferably, the intermediate core section is provided with a straight memory in the austenite phase, although other shapes may be suitable for many situations.

One presently preferred method of heating the intermediate core member is by resistance or inductive heating. In this case, one electrical conductor is electrically connected by its distal end to a location in the proximal extremity of the intermediate core section and a second electrical conductors is electrically connected by its distal end to a location in the distal extremity of the intermediate core section. The proximal ends of the electrical conductors are electrically connected to a source for electrical energy by means of a suitable electrical connector. Upon passage of electrical current through the intermediate core section, its temperature rises by the resistive or inductive heating to the desired transformation temperature. The intermediate core section should be otherwise electrically isolated to avoid loss of current, to prevent undesirable heating of adjacent guidewire components and the delivery of electrical current to adjacent tissue. Preferably, one or more temperature sensor or other means are provided on or in association with the intermediate core section to sense the temperature and facilitate the control thereof by controlling the level of electrical current directed to the intermediate core section. Conventional control procedures and systems may be employed to effect this temperature control.

The intermediate core section with substantial levels of the martensite phase provides excellent flexibility to the distal part of the guidewire which allows the guidewire to pass through tortuous passageways without undergoing plastic deformation or causing traumatic engagement with the wall of a body lumen through which the guidewire is passing. The martensite of the intermediate core section is transformed when the guidewire is in the desired location within the patient's body lumen and in this condition the intermediate core section has a higher strength level provided by the austenite phase so there is little tendency for the distal part of the guidewire to be displaced from, e.g. pulled out of, a side branch of a coronary artery when a catheter is advanced over the guidewire.

The alloy composition and the thermomechanical processing of the intermediate core section are selected to provide an austenite phase during the mechanical working of the intermediate core section and then the memory inducing heat treatment is selected to provide a martensite phase at the operating temperature of the guidewire, i.e body temperature, with a transformation temperature (to the austenite phase) not greater than about 50° C., preferably not greater than about 45° C.

The intermediate core section is preferably formed from an alloy consisting essentially of about 30 to about 52% titanium and the balance nickel and up to 10% of one or more additional alloying elements. Such other alloying elements may be selected from the group consisting of up to 3% each of iron, cobalt, platinum, palladium and chromium and up to about 10% copper and vanadium. As used herein all references to percent composition are atomic percent unless otherwise noted. The presently preferred alloy composition is about 51% nickel with the balance being titanium and conventional impurities.

To form the intermediate section of the guiding member, elongated member of the preferred alloy material is first cold worked, preferably by drawing, to effect a size reduction of about 30% to about 70% in the transverse cross-section thereof. The cold-worked material may then be given a memory imparting heat treatment at a temperature of about 450° to 600° C. for about 0.5 to about 60 minutes, while maintaining a longitudinal stress on the elongated portion equal to about 5% to about 50%, preferably about 10% to about 30%, of the yield stress of the material (as measured at room temperature). This thermomechanical processing imparts a straight "memory" to the superelastic portion and provides a relatively uniform residual stress in the material. Another method providing similar properties involves mechanically straightening the wire after the cold work and then heat treating the wire at temperatures between about 300° and about 450° C., preferably about 330° to about 400° C. However, this latter treatment provides substantially higher tensile properties. Finish austenite transformation temperature is preferably less than body temperature and generally about −10° C. to about 30° C. For more consistent final properties, it is preferred to fully anneal the solid rod or tubular stock prior to cold work so that the material will always have the same metallurgical structure at the start of the cold working and so that it will have adequate ductility for subsequent cold working. It will be appreciated by those skilled in the art that means of cold working the metal other than drawing, such as rolling or swaging, can be employed.

The cold-worked and heat-treated NiTi alloy material is in the austenite phase at the temperature at which the intermediate core section is to be mechanically worked, e.g. centerless grinding to the final diameter or to form tapers therein. Effective grinding of the intermediate core section is difficult when the alloy has substantial levels of the martensitic phase, but it is quite easy when the work piece is in the austenite phase.

After the final mechanical working of the intermediate core section, it is subjected to a low temperature aging treatment at about 375° to about 450° C. for at least 15 minutes, preferably about 0.5 to about 12 hours to ensure a martensite phase with a finish austenite phase transformation temperature above body temperature but less than 50° C. For an alloy comprising about 51 atomic % nickel and the balance titanium, a low temperature aging treatment of 400° C. for two hours provides an austenite start temperature of 30° C., a austenite peak temperature of 38° C. and an austenite finish temperature of 44° C., and a martensite start temperature of 38° C. a martensite peak temperature of 34° C. and a martensite finish temperature of 25° C.

In one presently preferred embodiment, the intermediate core section and the distal core section are initially formed from the same starting NiTi workpiece. After the workpiece has been cold worked and heat treated to the austenite phase in the prescribed manner and then further mechanically formed to the final desired shape, e.g. by centerless grinding, the intermediate and distal core sections are separated by suitable cutting means. The intermediate core section is subjected to the low temperature aging treatment to generate the martensite phase which is stable at body temperature. The separated distal core section, which is used in the austenite phase, is assembled without further processing into the guidewire. The proximal and distal core sections are preferably connected to proximal and distal ends of the intermediate section respectively, by means of a cylindrical shaped tubular connector element which is formed of essentially the same NiTi alloy with superelastic properties to provide a smooth transition between the proximal and intermediate core sections and the intermediate and distal core sections.

These and other advantages of the invention will become more apparent from the following detailed description thereof when taken in conjunction with the following exemplary drawings.

DETAILED DESCRIPTION OF THE INVENTION

FIGS. 1–4 illustrate a guidewire 10 which embodies features of the invention. Generally, the guidewire 10 includes a elongated shaft 11 with a proximal core section 12, an intermediate core section 13 and a distal core section 14. A helical coil 15 is disposed about the distal core section 14 and is secured by solder or adhesive at locations 16 and 17. A shaping ribbon 18 is secured by its proximal end to the distal core section 14 at location 17 and by its distal end to the distal end of the helical coil 15 by welding or brazing forming the rounded end 19 in a conventional "floppy" construction.

Figure 1:
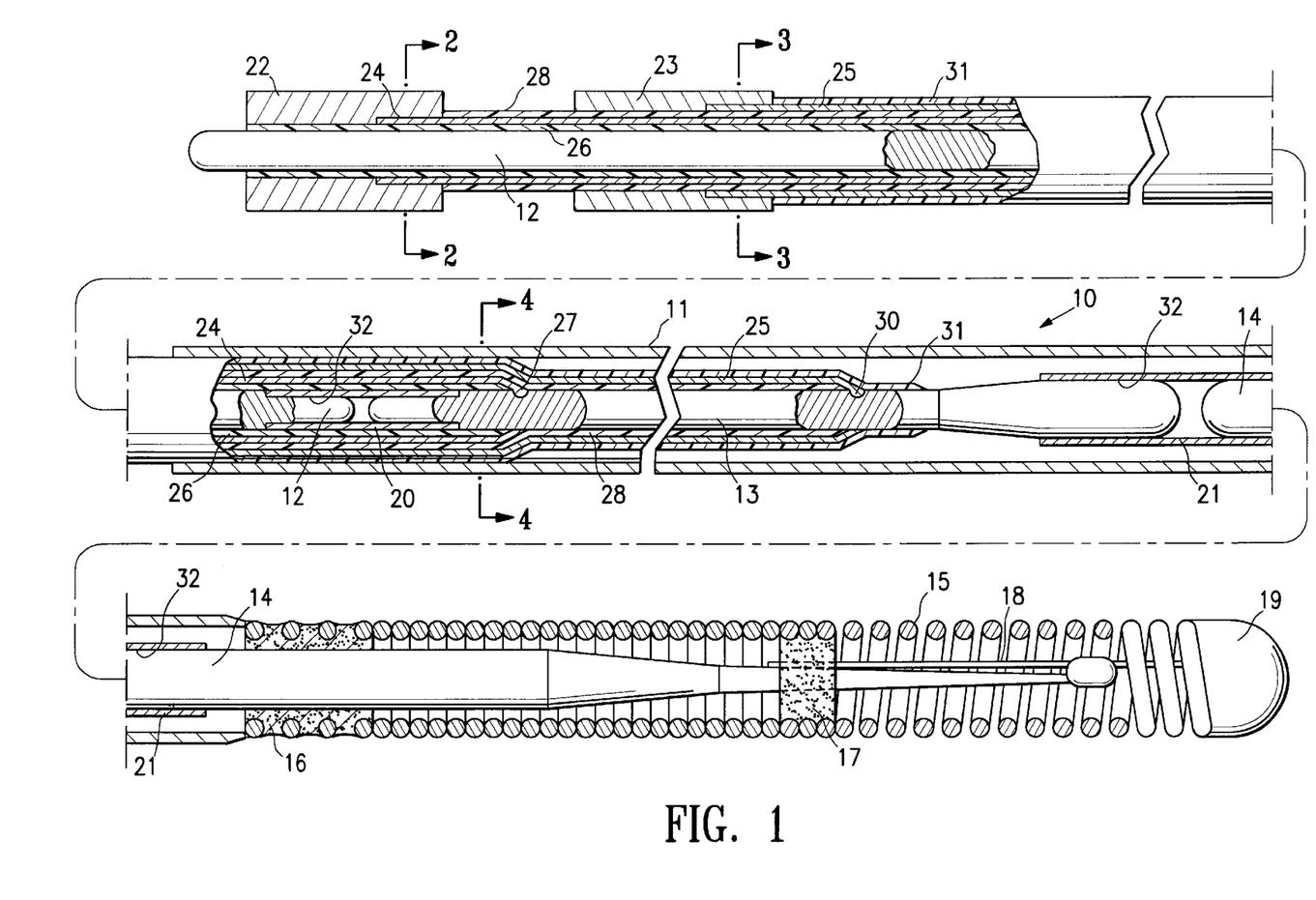
FIG. 1 is an elevational view, partially in section, of a guidewire having features of the invention.
Figure 2:
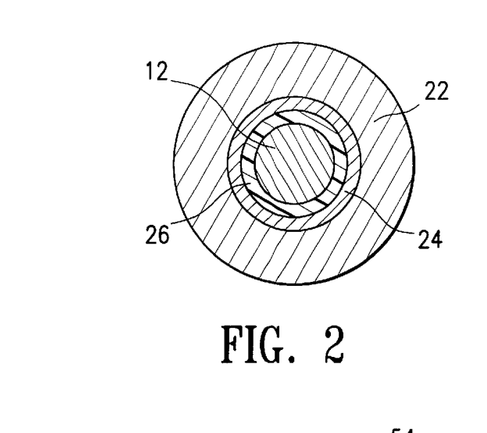
FIG. 2 is a transverse cross-sectional view of the guidewire shown in FIG. 1 taken along the lines 2—2.
Figure 3:
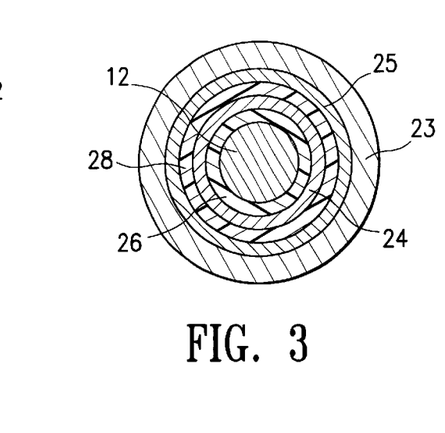
FIG. 3 is a transverse cross-sectional view of the guidewire shown in FIG. 1 taken along the lines 3—3.
Figure 4:
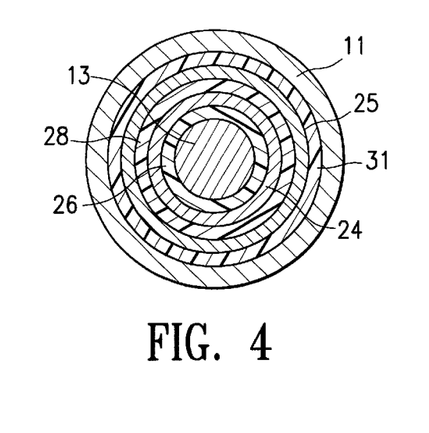
FIG. 4 is a transverse cross-sectional view of the guidewire shown in FIG. 1 taken along the lines 4—4.

A first cylindrical connector member 20 interconnects the distal end of the proximal core section 12 and the proximal end of the intermediate core section 13. A second cylindrical connector member 21 interconnects the distal end of the intermediate core section 13 and the proximal end of the distal core section 14. The first and second cylindrical connector members 20 and 21 may be secured to the respective core sections by a suitable adhesive or by solder. The intermediate and distal core sections 13 and 14 and the connector members 20 and 21 are formed of a NiTi alloy which generates a titanium oxide surface making the soldering difficult. However, these members can be effectively soldered by removing the oxide layer and pre-tinning the nascent surface with a gold-tin solder as described in U.S.

Pat. No. 5,341,818 (Abrams et al.) which is incorporated herein by reference.

The proximal core section 12 is provided with a pair of electrodes 22 and 23 which are in electrical contact with conducting layers 24 and 25 respectively. Insulating layer 26, which is disposed on the surface of the proximal core section 12, electrically isolates the proximal core section from the electrode 22, and, as shown is FIG. 1, extends to the proximal end of the intermediate core section 13. The conducting layer 24 extends to location 27 on the proximal end of the intermediate core section 13 just beyond the end of the insulating layer 26 where it is in electrical contact with the surface of the intermediate core section at the said location.

An intermediate insulating layer 28 is provided on the surface of the conducting layer 25 which extends from the distal end of electrode 22 to the distal portion of the intermediate core section 13 and electrically isolates the electrode 23 from the conducting layer 24. The conducting layer 25 extends distally on top of the intermediate insulating layer 28 to a location 30 immediately beyond the distal end of the insulating layer 28 where it is in electrical contact with the surface of the intermediate core section. A third insulating layer 31 is disposed on the surface of the conducting layer 25 and extends from the distal end of the electrode 23 to beyond the location 30 to ensure complete insulation of the conducting layer 25. An insulating tubular member 32, formed of suitable material such as polyimide, is disposed on the inner surface of the cylindrical connecting member 21 to ensure that no electrical current can pass from the intermediate core section 13 to the distal core section 14. Both the insulating and conducting layers may be applied by dip coating, spraying or other suitable methods known to those skilled in the art. Interfitting tubular members of insulating and conducting materials may likewise be used.

Figure 5:
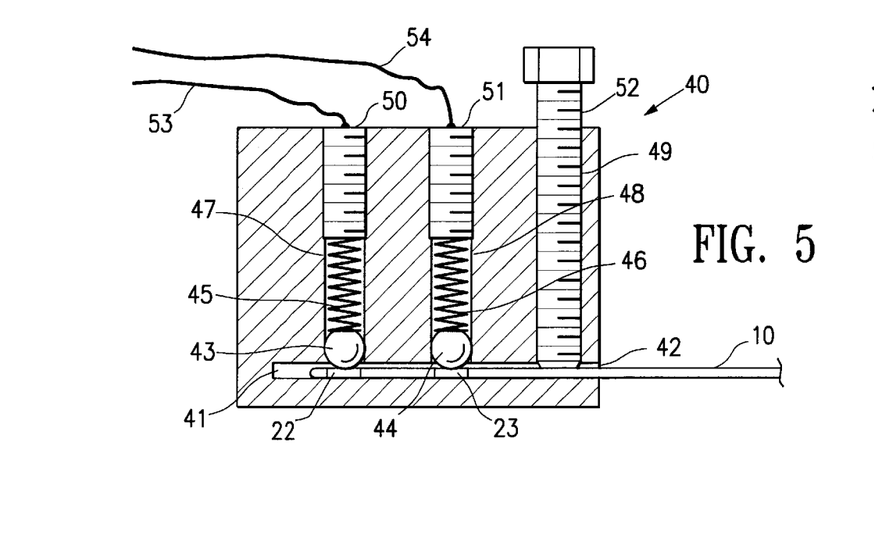
FIG. 5 is a longitudinal cross-sectional view of an electrical connector system which has inserted therein the proximal end of a guidewire such as that shown in FIG. 1 to provide electrical connection between the electrodes on the proximal end of the guidewire and an electrical source (not shown)
Figure 6:
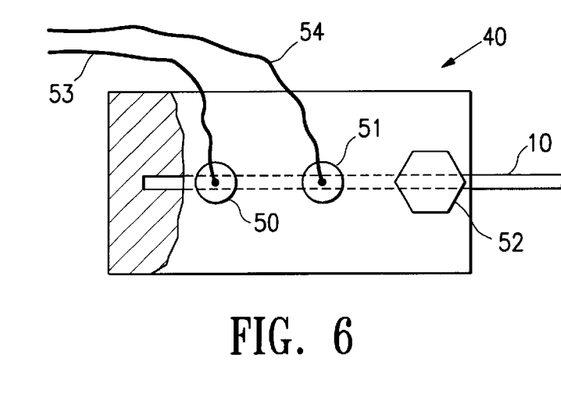
FIG. 6 is a top view, partially in-section, of the connector shown in FIG. 5.

FIGS. 5–6 schematically illustrate an electrical connector 40 for connecting the electrodes 22 and 23 on the proximal end of the guidewire 10 to a source of high frequency electrical energy (not shown). The connector 40 has an elongated passageway 41 extending inwardly from an exterior port 42 which is configured to slidably receive the proximal end of the guidewire 10. The connector 40 has a pair of electrical contacts 43 and 44 which are spaced along passageway 41 so as to be aligned with the electrodes 22 and 23 when the proximal end of the guidewire 10 is properly positioned within the passageway. The electrical contacts 43 and 44 are ball bearings which are urged into contact with the electrodes 22 and 23 by the biasing action of springs 45 and 46 disposed within the passageways 47 and 48 perpendicular with the passageway 41. Set screws 50 and 51 are threadably disposed within the upper threaded portions of the passageways 47 and 48 to engage the springs 45 and 46 to effect the biasing against the electrical contacts 43 and 44. A screw clamp 52 is threadably disposed within the threaded channel 49 to be tightened against the proximal end of the guidewire 10 to hold the guidewire in place and prevent its removal. Electrical conductors 53 and 54 are electrically connected by their distal ends to set screws 50 and 51 and by their proximal ends to a high frequency (e.g. RF) electrical energy source (not shown). The electrical power requirements for the system will vary depending upon the nature of the current transmission to the intermediate core section and the mass of the intermediate section. Generally, however, the power requirements will be within the range of about 3 to about 15 watts, usually about 6 to about 10 watts.

Figure 7:
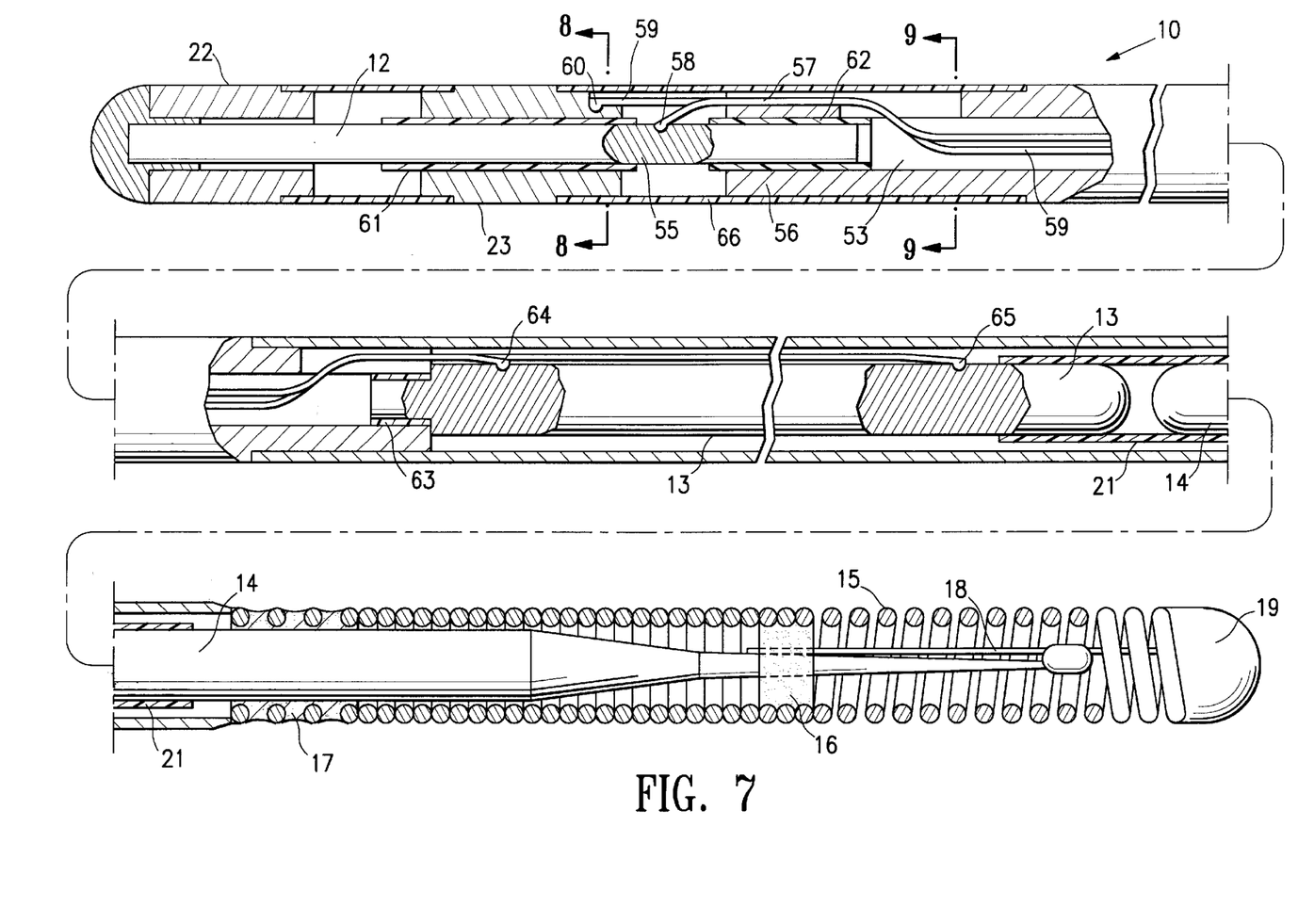
FIG. 7 is a longitudinal view, partially in section of an alternative embodiment of the invention.
Figure 8:
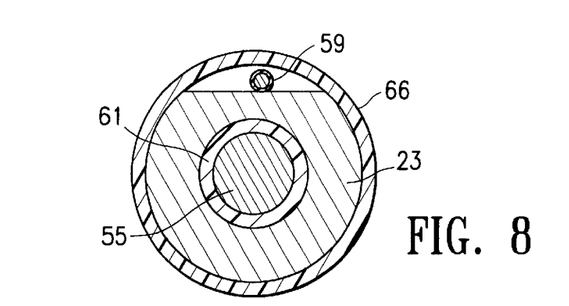
FIG. 8 is a transverse cross-sectional view of the guidewire shown in FIG. 7 taken along the lines 8—8.
Figure 9:
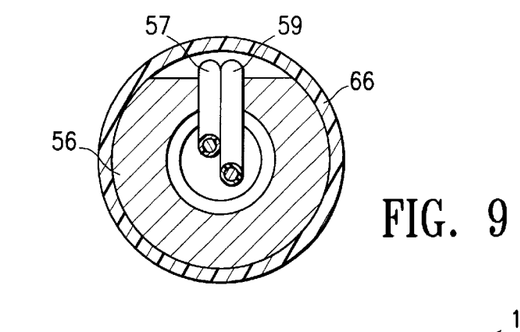
FIG. 9 is a transverse cross-sectional view of the guidewire shown in FIG. 7 taken along the lines 9—9.

An alternate embodiment of the invention is depicted in FIGS. 7–9. The proximal core section 12 of this embodiment has a solid core portion 55 and a tubular portion 56. Individually insulated electrical wire 57 is electrically connected by it proximal end at location 58 to the solid core portion 55 to which electrode 22 is electrically connected. Insulated electrical conducting wire 59 is electrically connected by its proximal end to electrode 23 at location 60. Insulating sheath 61 is disposed between the electrode 23 and the solid core portion 55. An insulating sheath 62 is disposed between the proximal end of the tubular portion 56 and the solid core portion 55 and insulating sheath 63 is disposed between the tubular portion 56 and the intermediate core section 13 to electrically isolate the tubular portion. Polyimide is a suitable material for the sheaths 61, 62 and 63. The conductor wire 57 is electrically connected by its distal end to the proximal end of the intermediate core section 13 at location 64 and electrical conducting wire 59 is electrically connected by its distal end to the distal portion of the intermediate section 13 at location 65. A polymer sleeve 66 is disposed over the junction between the solid core portion 55 and the tubular portion 56. The distal end of the guidewire 10 has essentially the same structure as that shown in FIG. 1 and is numbered accordingly.

Figure 10:
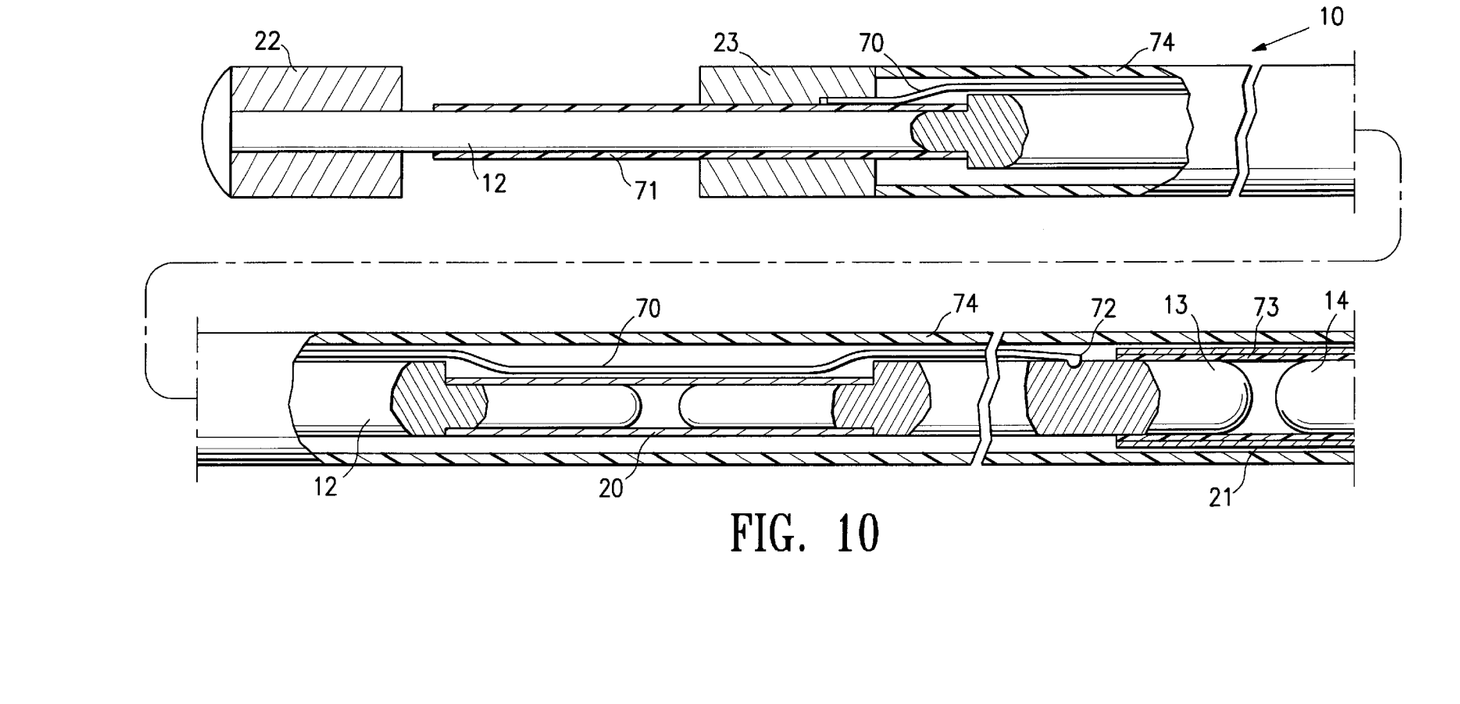
FIG. 10 is a partial elevational view, partially in section, of an alternative embodiment of the invention.

FIG. 10 depicts another alternate embodiment of the invention wherein the guidewire 10 has the proximal electrode 22 electrically connected to the proximal core section 12, and an individually insulated conductor wire 70 is electrically connected to the distal electrode 23. Electrical connection between the distal-end of the proximal core section 12 and the proximal end of the intermediate core section 13 is made by the cylindrical connector member 20. A first insulating layer 71 covers the exterior of the proximal core section 12 to insulate the latter from the electrode 23. Cylindrical connector 20 mechanically and electrically connects the distal end of the proximal core section 12 with the proximal end of the intermediate core section 13. The conductor wire 70 electrically interconnects the distal electrode 23 with the distal end of the intermediate section 13 at location 72. An insulating sleeve 73 is disposed about the distal end of the intermediate section and the proximal end of the distal core section 14 within the cylindrical connector member 21 to electrically isolate the distal core section from the intermediate core section. An outer polymer jacket 74 is provided over a substantial part of the guidewire shaft 11 distal to the electrode 23.

Figure 11:
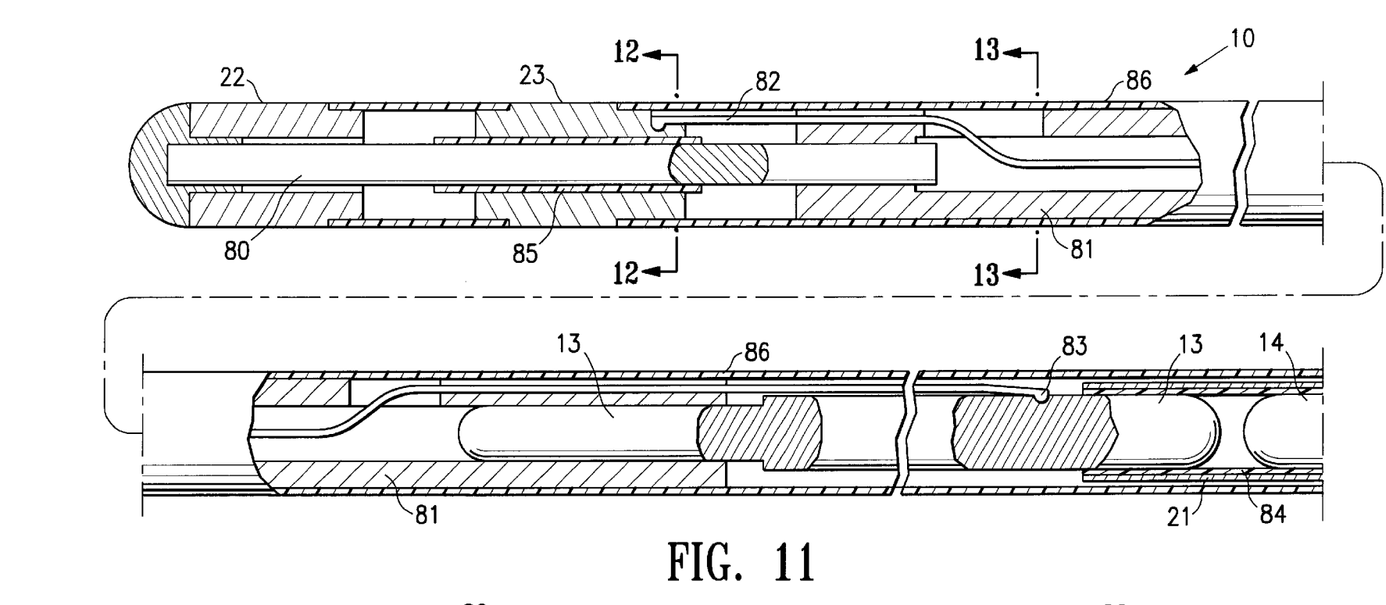
FIG. 11 is a partial elevational view, partially in section, of another alternative embodiment of the invention.
Figure 12:
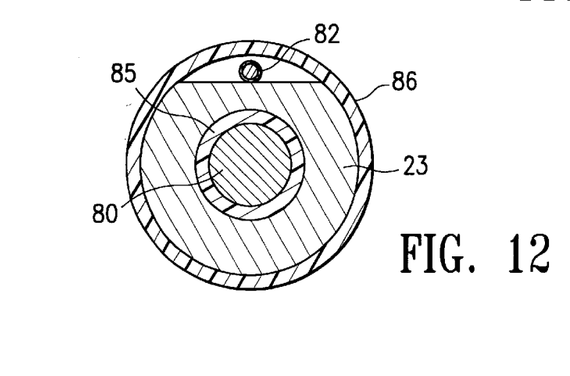
FIG. 12 is a transverse cross-sectional view of the guidewire shown in FIG. 11 taken along the lines 12—12.
Figure 13:
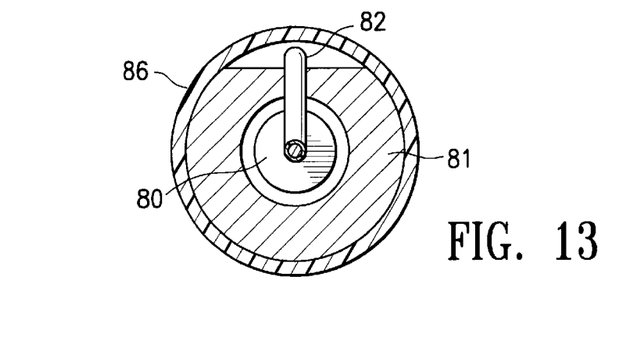
FIG. 13 is a transverse cross-sectional view of the guidewire shown in FIG. 11 taken along the lines 13—13.

Yet another embodiment of the invention is illustrated in FIGS. 11–13 which is similar to both of the prior alternate embodiments. In this embodiment the proximal core section has a proximal solid core portion 80 with a distal tubular portion 81 which is electrically and mechanically connected to the solid core portion. Electrode 22 of the guidewire 10 is electrically connected directly to the solid core portion 80. Distal electrode 23 is electrically connected to the proximal end of individually insulated electrical conductor wire 82 which has its distal end connected to the distal end of the intermediate core section 13 at location 83. Insulating layer 84 is disposed about the distal end of the intermediate core section and the proximal end of the distal core section and is disposed between these ends and the cylindrical connector member 21. Insulating layer 85 is disposed between the solid core portion 80 and the electrode 23. An outer jacket 86 is provided about the exterior of the guidewire distal to the electrode 23. The distal portion of the guidewire 10 is essentially the same as in the prior embodiments.

The overall dimensions of the guidewire are generally about 140 to about 190 cm in length, typically about 175 cm, and about 0.008 to about 0.035 inch (0.89 mm) in diameter. The transverse dimensions of the intermediate and distal core sections may be substantially smaller than the transverse dimensions of the proximal core section. The intermediate core sections has a length of about 15 to about 40 cm, preferably about 20 to about 30 cm, and the distal core section is about 3 to about 15 cm, preferably about 4 to about 7 cm. The distal core section may have one or more tapers and the most distal part is preferably flattened, e.g. 0.002× 0.003 inch (0.05–0.075 mm) and 0.001×0.003 inch (0.025–0.075 mm). To the extent not otherwise described, conventional construction techniques and materials may be utilized.

The intermediate core section is formed of a shape memory NiTi alloy as previously described and at operating temperature (37° C.) is in the martensite phase. The preferred alloy composition is about 51% (atomic) nickel and the balance titanium and conventional impurities. The distal core section 14 is preferably formed from the same alloy but in the austenite phase at operating temperature.

The guidewire of the invention is utilized in essentially the same fashion as conventional guidewires, except that after placement of the guidewire at a desirable location within the patient's body lumen, but before a catheter is advanced over the distal portion of the guidewire, the intermediate core section is heated to a temperature which transforms a substantial portion, preferably all, of the martensite phase to the austenite phase. While it is usually desirable to convert all of the martansite phase of the intermediate core section to the austenite phase, total conversion is not necessary to obtain the advantages of the invention. However, usually at least 50% of the martensite phase must be converted to provide the strength desirable to facilitate effective tracking of a catheter over the inplace guidewire. The guidewire must be long enough for its distal end to extend out the distal end of the catheter to be advanced over the guidewire and it proximal end with the electrodes to enable the electrodes thereon to be electrically connected to a high frequency electrical energy source.

A variety of modifications and improvements may be made to the present invention without departing from the scope thereof. Although individual features of embodiments of the invention may be shown in some of the drawings and not in others, those skilled in the art will recognize that individual features of one embodiment of the invention can be combined with any or all the features of another embodiment.

What is claimed is:

1. A method of performing an intraluminal procedure within a patient's body lumen comprising:
   a) providing a guidewire which has a distal core section and an intermediate core section, the intermediate core section having proximal and distal ends and being formed of a NiTi alloy with a substantial level of martensite phase at body temperature and with a final austenite transformation temperature above body temperature but below 50° C. and the distal core section which has proximal and distal ends and which is secured by its proximal end to the distal end of the intermediate core section and which is electrically isolated from the intermediate core section;
   b) positioning the guidewire at a desirable location within the patient's body lumen;
   c) heating the intermediate core section to a temperature above body temperature to convert at least part of the martensite phase of the intermediate core section to the austenite phase; and
   d) advancing a catheter over the intermediate core section of the guidewire while the intermediate core section is predominantly in the austenite phase to a desired location within the patient's body lumen.

2. The method of claim 1 wherein at least 50% of the martensite phase in the intermediate core section is converted to the austenite phase when the intermediate core section is heated within the body lumen.

* * * * *